United States Patent [19]

Genese

[11] 4,014,330
[45] Mar. 29, 1977

[54] DISPOSABLE TWO-COMPARTMENT SYRINGE

[75] Inventor: Joseph Nicholas Genese, Waukegan, Ill.

[73] Assignee: Abbott Laboratories, North Chicago, Ill.

[22] Filed: Oct. 28, 1975

[21] Appl. No.: 626,020

[52] U.S. Cl. .................... 128/218 M; 128/272.1
[51] Int. Cl.² ..................................... A61M 5/00
[58] Field of Search ... 128/218 M, 218 DA, 218 D, 128/218 P, 218 R, 218 N, 218 NV, 215, 216, 272.1, 220, 221

[56] References Cited

UNITED STATES PATENTS

| | | | |
|---|---|---|---|
| 3,489,147 | 1/1970 | Shaw | 128/218 M |
| 3,724,460 | 4/1973 | Gomez et al. | 128/218 M |
| 3,810,469 | 5/1974 | Hurschman | 128/218 M |
| 3,835,855 | 9/1974 | Barr, Jr. | 128/218 M |
| 3,946,732 | 3/1976 | Hurscham | 128/218 M |

*Primary Examiner*—John D. Yasko
*Attorney, Agent, or Firm*—Robert L. Niblack; Neil E. Hamilton

[57] ABSTRACT

A prefilled, readily activated disposable syringe wherein a fluid medicament is sealed in a syringe barrel by means of a puncturable sealing element. The syringe barrel also accommodates a slidable piercing member which includes a piercing tubular member held out of contact with the puncturable sealing element until it is desired to intermix a second fluid material with the first. The slidable piercing member has a removable cap disposed thereon for sterile thumb contact and engagement means between the slidable member and the sealing element so that the slidable piercing member positively engages and pierces through the puncturable sealing element when it is desired to activate the syringe. A stoppered vial containing the second fluid is also pierced by the piercing tubular member and upon movement of the vial toward the punctured sealing element quick and efficient mixing of the two fluid materials is effected as well as administration of the combined materials.

10 Claims, 5 Drawing Figures

DISPOSABLE TWO-COMPARTMENT SYRINGE

BACKGROUND OF THE INVENTION

This invention relates to a disposable syringe of the prefilled type. More particularly, it relates to a prefilled, disposable syringe wherein the medicament contained in the syringe is held under maximum sterile conditions until it is desired to premix it with a fluid material, the syringe then affording positive piercing sequencing by a sliding piercing member first with the medicament and subsequently the diluent and at the same moment, utilizing a minimum number of parts.

There are currently available many types of disposable syringes wherein a medicament is sealed in a syringe barrel to be later combined with a diluent for the material in the syringe barrel. There are also available unitary containers which contain a medicament and a diluent for it in two different compartments which are then intermixed prior to their usage. However, many of the devices which are now available either do not afford positive intermixing between the two materials, are costly to manufacture because of the necessity of utilizing many component parts, are complicated in their usage because of many parts being involved or after intermixing in a container still require a syringe for injection. For example, in U.S. Pat. Nos. 2,684,068; 3,098,483 and 3,327,710, combination hypodermic syringes and mixing containers are disclosed. However, these units do not afford complete separation of one of the materials to be mixed from the piercing cannula or tube so that sterility and complete mixing can be a problem. Further, many of these units as well as one of the units described in U.S. Pat. No. 3,542,023 do not afford positive engagement and sequencing of the various compartments for the components to assure their intermixing. Positive intermixing is also a factor in U.S. Pat. No. 3,724,460 which while employing a multitude of components still does not afford a positive sequencing action in the unit. In U.S. Pat. Nos. 3,489,147 and 3,477,432, multicomponent combination mixing and administration syringes are disclosed. However, various manipulations of these units must be made as well as an undesirable cost factor in manufacturing a double-barreled type syringe.

It is an advantage of the present invention to afford a novel combined mixing and hypodermic syringe which affords maximum isolation and sterility of two components which are to be ultimately mixed and positive sequencing of the intermixing. Other advantages are a syringe which requires a minimum number of parts, minimum manipulations, preassembly of certain components without accidental engagement and a syringe system which utilizes a minimum amount of space for packaging.

SUMMARY OF THE INVENTION

The foregoing advantages are accomplished and the shortcomings of the prior art are overcome by the present prefilled, readily activated and disposable syringe which has the usual barrel and nozzle except that the barrel is very short in length. A puncturable sealing element seals a quantity of fluid material in the syringe barrel and a slidable piercing member is positioned in the syringe barrel and spaced from the puncturable sealing element. Means are carried by the piercing member and the puncturable sealing element to position a piercing point in the slidable piercing element a distance away from and in nonpiercing contact with the sealing element and at a later time to effect positive engagement between them. Upon movement of the slidable piercing member toward the sealing element, the puncturable sealing element will be pierced and a positve engagement encountered between the puncturable sealing element and the slidable piercing member. A stoppered vial will then engage the opposing end of the slidable piercing member and be placed in fluid contact with the fluid medicament which was previously sealed by the puncturable sealing element. Removable caps are placed on the nozzle member as well as on the slidable piercing member so as to afford maximum sterility. The removable cap will be retained on the nozzle as the vial is moved into the syringe barrel to effect intermixing of the fluid material therein with the fluid medicament. After thorough intermixing, the cap is removed from the nozzle and a hypodermic needle engaged thereon with the syringe then being employed in the normal usage of a hypodermic syringe. In a preferred manner, certain interlocking means are employed at opposing ends of the slidable piercing member to afford positive engagement with the puncturable sealing element as well as with a stopper in the vial.

BRIEF DESCRIPTION OF DRAWING

A better understanding of the present prefilled, readily activated syringe will be afforded by reference to the drawing wherein.

DESCRIPTION OF THE PREFERRED EMBODIMENT

Figure 1:
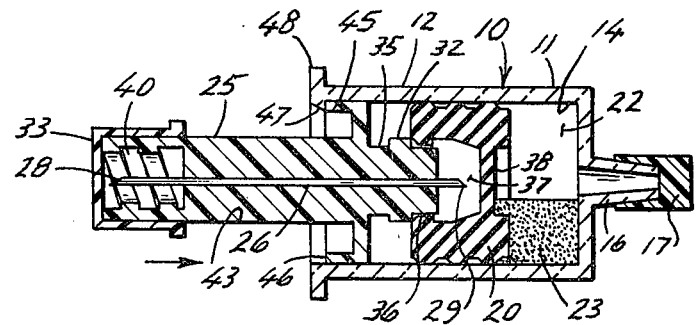
FIG. 1 is a view in vertical section showing a portion of the hypodermic syringe of this invention in a prepackaged condition.
Figure 5:
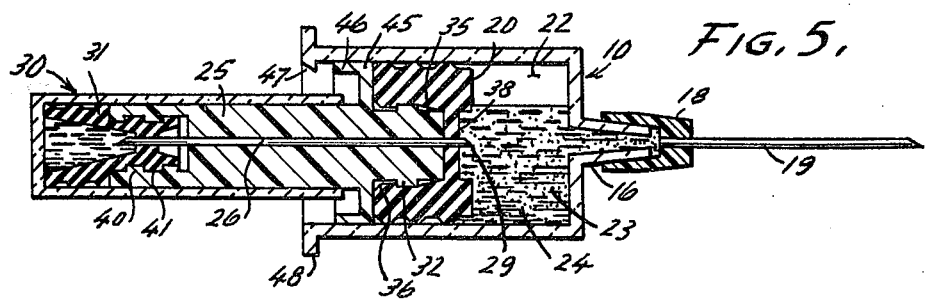
FIG. 5 is a view similar to FIG. 4 except showing the attachment of the hypodermic needle prior to the usage of the syringe.

The prefilled, readily activated syringe generally 10 is composed of the usual barrel 11 forming a tubular chamber 12 with internal wall 14. A nozzle member 16 extends from one end of the syringe barrel and is covered by a removable cover or cap 17. As best seen in FIG. 5, when cap 17 is removed it is replaced by a hypodermic needle 19 which by means of adapter 18 is positioned on nozzle 16. Disposed in barrel 11 is a puncturable sealing element 20 and is spaced from nozzle 16 to provide a compartment 22 for a flowable medicinal agent 23 preferably in the form of a powder. As best seen in FIG. 1, a slidable piercing member 25 with a central piercing tubular member 26 has an extended portion 35 with an annular member 32 positioned adjacent an annular orifice 36 of puncturable sealing element 20 but out of contact therewith. Further, piercing point 29 will be positioned so that it will not pierce diaphragm section 38 until annular member 32 passes through orifice 36.

Figure 2:
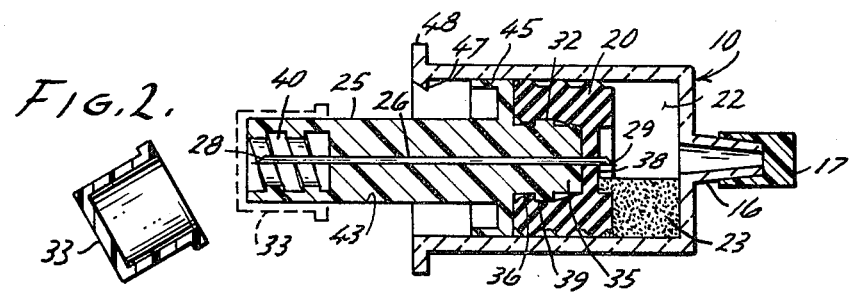
FIG. 2 is a view similar to FIG. 1 except showing the unit in its next stage of operation with the slidable piercing member piercing through the sealing means and removal of the cap prior to engagement with a stoppered vial.

As best indicated in FIG. 2, when the slidable piercing member 25 is moved to a greater degree into barrel 11 so that guide 45 engages the puncturable sealing element 20, piercing point 29 will then pass through diaphragm section 38 and at the same moment the annular member 32 on extended portion 35 of the slidable piercing member 25 will pass through annular orifice 36 and engage the opposing sides thereof as shown at 39. It will be noted that the opposing end of slidable piercing member 25 has a portion with internal threads 40 which are covered by a removable cap 33.

Figure 3:
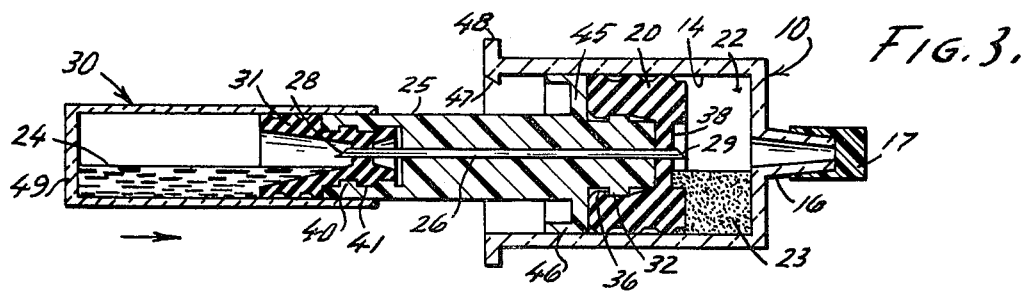
FIG. 3 is a view similar to the views in the previous Figures and showing the stoppered vial engaging the slidable piercing member.

As indicated in FIG. 3, a stoppered vial 30 having a stopper 31 has an external threaded portion 41 for engagement with the internal threads 40 of slidable piercing member 25. When these threads are completely engaged, piercing point 28 will be positioned inside of vial 30 so that communication will be made between the inside of vial 30 and compartment 22. As will also be noted, a barbed-type flange 47 extends from the internal wall 14 of barrel 11 and at open end thereof so as to form a temporary stop for guide 45 and its flanged portion 46. It will also be seen that barrel 11 is very short in longitudinal dimension, being shorter than vial 30. This aids in packing the unit as it takes little space.

OPERATION

A better understanding of the advantages of the readily activated, prefilled syringe 10 will be had by a description of the manner of its operation. Unit 10 will be packaged as indicated in FIG. 1 with the prefilled stoppered vial 30 preferably contained in the same package. The medicinal material 23 will in this instance be a powdered, flowable material such as a general anesthetic. It will be noted that the medicinal material 23 will be held in a sterile condition by means of puncturable sealing element 20 and sealing cap 17. Further protection for the sterility of the unit is afforded by means of protective cap 33 enclosing piercing point 28 of the piercing tubular member 26 as well as the aspect that the piercing tubular member 26 is held out of contact with compartment 22 containing the sterile medicinal powder 23. Sterility is also assured by the fact that annular member 32 is in contact with annular orifice 36 of puncturable sealing element 20 so that piercing point 29 is out of contact with the outside atmosphere.

Figure 4:
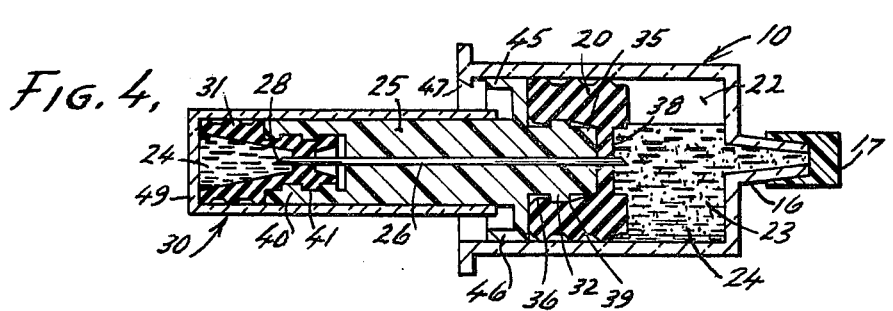
FIG. 4 is a view similar to the views in the previous Figures and showing the next step in usage of the syringe with the fluid material in the vial being transferred and mixed with the medicament in the syringe barrel.

When it is desired to utilize unit 10, all that is required is the movement of the slidable piercing member 25 into barrel 11 by means of finger and thumb pressure on external flange 48 and protective cap 33 to move the slidable piercing member 25 in the position shown in FIG. 2 with guide 45 abutting against puncturable sealing element 20 which is afforded by annular member 32 passing through orifice 36 with the placement of annular member 32 to the inside of the annular orifice 36 as shown at 39. In this position, piercing point 29 will be in communication with compartment 22 and the medicinal agent 23 with sealing element 20 locked to piercing member 25. Subsequently, cap 33 will be removed and vial 30 attached to the slidable piercing member 25 by means of the external threads 41 of stopper 31 engaging the internal threads 40 of slidable piercing member 25. The unit will then be as it appears in FIG. 3, which will place piercing point 28 in communication with the contents of vial 30 and fluid material 24 which preferably will be a solvent or diluent for the powder medicinal agent 23. The next sequence of operation will be the movement of vial 30 over the slidable piercing member 25 to thereby force the fluid material 24 through the piercing tubular member 26 and into compartment 22 to effect a mixing of the diluent 24 with the medicinal agent 23. This motion will continue until stopper 31 of the vial contacts the end wall 49 of vial 30 as shown in FIG. 4. Suitable mixing of the diluent 24 and the powder 23 can be additionally effected by shaking the unit 10 with the cap 17 still in place. It should be noted in comparing FIGS. 3 and 4, that in FIG. 4 sealing element 20 will move a short distance away from nozzle 16 due to the increased volume of material in compartment 22. The next step will be the removal of cap 17 and the fitting of hypodermic needle 19 by means of needle adapter 18 onto nozzle 16. Injection of the medicinal material 23 will then be effected in the usual manner.

In the foregoing description, an annular member 32 is utilized to prevent the piercing point 29 of piercing tubular member 26 from pre-engaging the diaphragm 38 and consequently, the compartment 22 containing the medicinal material. However, intentional force moves this annular member 32 through the restricted orifice 36. Other force fitment, of course, could be utilized such as a multiplicity of barbs for a tight friction fit between the slidable piercing member 25 and sealing element 20 which would become effective after the needle point 29 passes through the diaphragm section 38. Further, a threaded arrangement indicated by threads 40 and 41 is employed to position vial 30 onto slidable piercing member 25. Although this particular arrangement is preferred, it could be replaced by friction fit between stopper 31 and an end portion of slidable piercing member 25 with a portion of piercing tubular member 26 exposed. Also, if desired, needle 19 with adapter 18 could be placed on nozzle 16 at the time the unit is packaged as shown in FIG. 1. However, the needle 19 will then have to have a tight sealing cap to cover it and there is the risk that powder material would gain entry to the needle and not become uniformly mixed with the diluent or solvent prior to administration.

The preferred materials for composing barrel 11 and vial 30 is glass. Housing 43 for piercing tubular member 26 as well as caps 17 and 33 are formed from a resinous plastic material with stoppers 20 and 31 being formed of a resilient pierceable rubber or plastic material. If desired, the syringe barrel 11 could be formed from a clear or translucent plastic material as could the vial 30.

It will thus be seen that through the present invention there is now provided a prefilled, readily activated, sterile syringe system which involves a minimum number of parts and a minimum number of manipulative steps for its utilization. Positive sequential operation of the two-phase syringe system is afforded while accidental activation is avoided. The syringe unit can be fabricated with existing parts and without extensive molding fabrication.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A prefilled, readily activated syringe comprising:
   a barrel member defining a substantially tubular chamber having an internal wall section;
   means defining a nozzle member communicating with said tubular chamber for attachment with a cover in one instance, and a hypodermic needle in another instance;
   a puncturable sealing element in sealing engagement with the internal wall section of said barrel member and spaced from said nozzle member to provide a compartment for a medicinal material;
   a slidable piercing member disposed in said syringe barrel and spaced from said puncturable sealing element, said piercing member comprising:
   a piercing tubular member having oppositely disposed piercing points;
   force fitment means carried by said piercing member and said puncturable sealing element to position one of said piercing points in nonpiercing contact with said sealing element and upon slidable movement of said slidable piercing member toward said puncturable sealing element; to lock said piercing member in pierceable engagement and in communication with said compartment;
   a stoppered container containing a fluid material constructed and arranged to be engaged by another piercing point of said piercing member and pierced thereby to provide communication with the contents of said container;
   protective covers in sealing engagement with said nozzle member and said other piercing point, whereby with said piercing member and said one piercing point spaced from said puncturable sealing element, movement of said slidable piercing member toward said sealing element will effect a first piercing of said puncturable sealing element and locking engagement with said sealing element as well as communication with said compartment and with positioning of said stoppered container in a second independent piercing engagement with said other piercing point of said piercing member, fluid communication between said stoppered container and said compartment is established with movement of said container toward said piercing member effecting a flow of said fluid material into said compartment with a resulting mixing thereof and further movement of said vial toward said puncturable sealing element will effect an expelling of said mixture from said nozzle member.

2. The prefilled, readily activated syringe as defined in claim 1 wherein said force fitment means carried by said piercing member and said puncturable sealing element to position one of said piercing points in nonpiercing contact with said sealing element and to lock said piercing member and sealing element together is an extended portion on said piercing member and surrounding said tubular member, an annular member projecting from said extended portion, a chamber in said puncturable sealing element constructed and arranged to receive a section of said annular portion, said chamber defined by an annular orifice presenting an engagement surface when said annular member of said extended portion is positioned in said chamber.

3. The prefilled, readily activated syringe as defined in claim 2 wherein said puncturable sealing element comprises a pierceable diaphragm section forming an end of said chamber for receiving said extended portion of said piercing member.

4. The prefilled, readily activated syringe as defined in claim 3 wherein said stoppered container comprises a vial and said piercing member adjacent said other piercing point and said vial stopper have means for interlocking said piercing member and said vial stopper.

5. The prefilled, readily activated syringe as defined in claim 1 wherein said stoppered container is a vial and said barrel member is constructed and arranged with a shorter longitudinal dimension than said vial.

6. The prefilled, readily activated syringe as defined in claim 4 wherein said slidable piercing member further includes a housing member partially enclosing said piercing tubular member with said tubular member disposed in a stationary manner in said housing, said housing adapted to receive said vial thereover.

7. The prefilled, readily activated syringe as defined in claim 6 wherein said slidable member includes a sealing guide member for contact with said puncturable sealing element.

8. The prefilled, readily activated syringe as defined in claim 7 wherein said sealing guide member and said annular member on said projection of said piercing member are constructed and arranged to contact said annular orifice of said puncturable sealing element on opposite sides thereof.

9. The prefilled, readily activated syringe as defined in claim 1 wherein said vial is composed of a container with rigid walls.

10. The prefilled, readily activated syringe as defined in claim 1 wherein said nozzle member is constructed and arranged to accommodate a needle adapter to position said hypodermic needle on said nozzle member.

* * * * *

UNITED STATES PATENT AND TRADEMARK OFFICE
CERTIFICATE OF CORRECTION

PATENT NO. : 4,014,330
DATED : March 29, 1977
INVENTOR(S) : Joseph Nicholas Genese It is certified that error appears in the above-identified patent and that said Letters Patent are hereby corrected as shown below:

In column 2, line 66, after the word "of" please insert --chamber 37 in--.

Signed and Sealed this

Eighteenth Day of October 1977

[SEAL]

Attest:

RUTH C. MASON
Attesting Officer

LUTRELLE F. PARKER
Acting Commissioner of Patents and Trademarks